US011857180B2

(12) United States Patent
Venturini et al.

(10) Patent No.: US 11,857,180 B2
(45) Date of Patent: *Jan. 2, 2024

(54) ORTHOPAEDIC STAPLER (71) Applicant: Orthofix S.R.L., Bussolengo (IT)

(72) Inventors: Daniele Venturini, Veronese (IT);
Denis Lorenzini, Veronese (IT);
Federico Vicenzi, Verona (IT)

(73) Assignee: ORTHOFIX S.R.L., Bussolengo (IT)

( * ) Notice: Subject to any disclaimer, the term of this patent is extended or adjusted under 35 U.S.C. 154(b) by 30 days.

This patent is subject to a terminal disclaimer.

(21) Appl. No.: 17/040,740

(22) PCT Filed: Mar. 18, 2019

(86) PCT No.: PCT/EP2019/056664
§ 371 (c)(1),
(2) Date: Sep. 23, 2020

(87) PCT Pub. No.: WO2019/185383
PCT Pub. Date: Oct. 3, 2019

(65) Prior Publication Data
US 2021/0015482 A1    Jan. 21, 2021

(30) Foreign Application Priority Data

Mar. 26, 2018 (IT) .................. 102018000003915

(51) Int. Cl.
A61B 17/064     (2006.01)
A61B 17/068     (2006.01)
(Continued)

(52) U.S. Cl.
CPC ...... A61B 17/0642 (2013.01); A61B 17/0682 (2013.01); A61B 17/8872 (2013.01);
(Continued)

(58) Field of Classification Search
CPC ... A61B 17/0642; A61B 17/068; A61B 17/10; A61B 17/17; A61B 17/8872;
(Continued)

(56) References Cited

U.S. PATENT DOCUMENTS

2009/0254090 A1* 10/2009 Lizee ................. A61B 17/0642
606/75
2012/0228355 A1*  9/2012 Combrowski ..... A61B 17/0642
227/175.1
(Continued)

FOREIGN PATENT DOCUMENTS

WO    2017/139315 A1    8/2017
WO    2017/139328 A1    8/2017

OTHER PUBLICATIONS

Nternational Searching Authority/European Patent Office, "International Search Report," for PCT/EP2019/056664 dated Jun. 5, 2019, 5 pages.
(Continued)

Primary Examiner — Marcela I. Shirsat
(74) Attorney, Agent, or Firm — HAYNES AND BOONE, LLP (57) ABSTRACT An orthopaedic stapler (1) comprising orthopaedic pliers (3) and an orthopaedic staple (2) integrally formed at the distal ends of the pliers (3). The orthopaedic staple (2) comprises a beam portion (4) and two insertion brackets (5) at the two opposite ends (6) of the beam portion (4) and substantially transverse with respect to the beam portion (4). The orthopaedic pliers (3) comprise two lever arms (12) integrally connected to the orthopaedic staple (2) by means of connection portions (15) at the two opposite ends (6) of the beam portion (4). The connection portions (15) are breakable along breakage sections (24). The lever arms (12) comprise at least one first projecting element (19), at least one second projecting element (20), the first projecting
(Continued)

element (19) on one lever arm (12) being directed towards the second projecting element (20) on the other lever arm (12). The first projecting element (19) and the second projecting element (20) are provided with a reciprocal engaging mechanism (21).

14 Claims, 4 Drawing Sheets (51) Int. Cl.
*A61B 17/88* (2006.01)
*A61B 17/115* (2006.01)
*A61B 90/00* (2016.01)
*A61B 17/00* (2006.01)

(52) U.S. Cl.
CPC .......... *A61B 90/03* (2016.02); *A61B 17/0644* (2013.01); *A61B 17/115* (2013.01); *A61B 2017/00473* (2013.01); *A61B 2017/0645* (2013.01); *A61B 2090/037* (2016.02)

(58) Field of Classification Search
CPC . A61B 17/0684; A61B 17/072; A61B 17/115; A61B 17/0644; A61B 17/07207; A61B 17/105; A61B 2017/00407; A61B 2017/00367; A61B 2017/0641; A61B 2017/0645; A61B 2017/07214; A61B 90/03; A61B 2090/037
USPC ............ 606/74–75; 227/175.1, 177.1, 178.1, 227/179.1, 901–902
See application file for complete search history.

(56) References Cited

U.S. PATENT DOCUMENTS

| | | | |
|---|---|---|---|
| 2016/0338697 A1* | 11/2016 | Biedermann | ...... A61B 17/0642 |
| 2017/0065275 A1 | 3/2017 | Cheney | |
| 2017/0273684 A1 | 9/2017 | Combrowski | |
| 2019/0046183 A1* | 2/2019 | Hartdegen | ......... A61B 17/0644 |

OTHER PUBLICATIONS

Nternational Searching Authority/European Patent Office, "Notification of Transmittal of the International Preliminary Report on Patentability," for PCT/EP2019/056664, dated Jun. 26, 2020, 28 pages.

* cited by examiner

ORTHOPAEDIC STAPLER

CROSS REFERENCE TO RELATED APPLICATIONS

The present application is the U.S. national phase of International Application No. PCT/EP2019/056664, filed Mar. 18, 2019, which designated the U.S. and claims priority to and the benefit of the Italian Application No. 102018000003915, filed Mar. 26, 2018, both of which are hereby incorporated by reference in their entirety as if fully set forth below in its entirety and for all applicable purposes.

FIELD OF APPLICATION

According to its more general aspect the present invention relates to the application of orthopaedic staples for immobilizing bone stumps in fractures and osteotomy operations.

The present invention relates essentially to the sector of devices employed in the traumatological and orthopaedical sector, in particular in cases involving fixing and stabilization of small bones.

PRIOR ART

As is well known in this specific technical sector, it is often necessary to use orthopaedic staples which are arranged on either side of a fracture or are used to ensure stabilization of an osteotomy. This requirement also arises in the treatment of a ruptured ligament or dislocated tendon in order to block the movement thereof.

The staples are in these cases disposable devices.

In particular, these devices are employed in foot surgery, a sector where the presence of a considerable number of small bones requires preferably the use of devices which are able to perform local immobilization of the fracture or osteotomy. In general, however, the recommended areas of use may be many, including arthrodesis fixation, bone fusion operations, as well as epiphysiodesis operations and orthopaedic operations involving remodelling of bone segments.

Since the function of the staple is to keep the bone stumps in correspondence of a fracture in contact in order to favour osteosynthesis, the staple is formed so as to generate a light pressure in the vicinity of the contact zone between the two stumps. For this purpose normally they have a beam portion connected at its ends to oppositely arranged insertion shanks or brackets.

The staples currently used may have various forms and sizes, depending on the specific application for which they are intended.

Typically they are U-shaped, but other profiled forms of the brackets, i.e. of the shanks inserted in the bone are possible, with a stepped, sawtooth or simply inclined form. The choice of form, as mentioned, depends on the particular application and anatomical site where the staple must be applied.

Moreover, in the case where the brackets have a toothed profile, it is evident that this solution is chosen in order to favour the insertion and at the same prevent unintentional removal of the bracket from the bone.

Also the form of the beam portion has been developed over time depending on the force which the staple must exert on the bone fragments.

Studies have also been carried on the materials which can be used and which may be chosen depending on the characteristics of the staple which are preferred to be optimized.

Often metallic materials are used, but different materials such as synthetic materials are also employed. For example, materials ranging from ordinary stainless steel which may be implanted, to titanium alloys, to plastic materials and nitinol are currently used.

Some known devices are made using shape memory materials in order to maximize the adaptive property of the staple to the type of fracture and the local anatomy of the patient. Moreover, these types of materials with superelastic properties are employed when it is required to ensure a constant compressed state of the bone stumps. This solution, however, is complex in terms of use, in particular requires the implant to be kept at specific temperatures before use. In any case, any material is treated so as to be completely sterile in view of the subcutaneous application of the device.

An important aspect during use of these devices is the instrument used to insert them and remove them. If, in fact, standard pliers are currently used to remove them, this is not the case for insertion. In this latter case the technique which is most commonly employed involves the pre-drilling and the pre-insertion of guide wires inside the seats for receiving the brackets, subsequent insertion of drilling guides and finally the insertion of the staple brackets. In many cases this insertion is performed using a special beater and a hammer.

This technique is obviously complex and requires the use of different instruments or a set of instruments composed of a plurality of components, something which affects both the ease of use and the overall cost of said instruments.

For example, orthopaedic staples with a known structure have a dedicated instrument for measuring the width of the staple needed for a given specific fracture.

US 2009/254090 A1 discloses a compression staple including two arms connected by a transverse bridge, each arm including an anchor portion and a manipulation portion connected by a separation mechanism or breakaway feature.

WO 2017/139315 A1 discloses a staple delivery device including a staple and an inserter, the inserter being movable between a free state and an actuated state, which moves consequently the staple. The inserter is connected to the staple by connections which can be ruptured after the staple has been implanted.

WO 2017/139328 A1 discloses a system for implant delivery including an implant and an inserter. The implant includes a body, retainers received in corresponding jaws of the inserter. When the implant is connected to the inserter and the inserter is actuated, the implant elastically deforms.

US 2017/273684 A1 discloses a surgical instrument including an implant, a grip, and a pre-set breaking point connecting the implant and the grip.

Although the devices present nowadays with the characteristic features which have been briefly described above ensure obvious advantages in terms of ease of use or in terms of particular adaptability to the specific case being treated, all of them have however common drawbacks, in particular as regards the staple implantation technique.

In fact, this implantation step, and in particular the step of inserting the brackets inside the respective seats formed beforehand in the bone, is even more complex. Furthermore, it is required to simplify further the step of releasing the staple inside the bone so as to ensure that the conditions defined by the surgeon and the consequent correct operation are maintained.

The technical problem forming the basis of the present invention is that of devising a new orthopaedic stapler having structural and functional features such as to be able to overcome the drawbacks of the solutions currently proposed by the prior art.

A further object is that of obtaining on the bone fragments a compressive pre-load which is generated and then assessed by the surgeon depending on the specific case.

Another object of the present invention is to obtain a device which may be used intuitively by any operator, with a greater or lesser degree of experience, ensuring the maximum ease of use.

SUMMARY OF THE INVENTION

The idea underlying the present invention is that of providing a device where the instrument for application of the staple and the staple itself are made as one piece which is formed so as to be able to adjust also only with one hand both the mode of insertion of the staple and the desired tensioning pre-load, with subsequent rapid release of the staple.

On the basis of this proposed solution the technical problem is solved by an orthopaedic stapler comprising orthopaedic pliers and an orthopaedic staple integrally formed at the distal ends of the pliers comprising a beam portion and two insertion brackets at the two ends of the beam portion, the brackets extending substantially in a direction transverse with respect to the beam portion. The orthopaedic pliers comprise two lever arms integrally connected to the orthopaedic staple by means of a connection portion at the two opposite ends of the beam portion. This connection portion is breakable along a breakage section. In short, the staple consists of a substantially U-shaped staple which is formed integrally at the ends of the insertion pliers, but may be easily removed since it is connected to the pliers by means of easy-breakage bridge-pieces. The lever arms comprise at least one first projecting element, at least one second projecting element, the first projecting element on one lever arm is directed towards the second projecting element on the other lever arm. The first projecting element and the second projecting element are provided with a reciprocal engaging mechanism.

Preferably, the reciprocal engaging mechanism comprises a sawtooth profile along the first projecting element and a corresponding sawtooth profile along the second projecting element (20).

In a preferred embodiment at least one lever arm comprises a ring portion at one end.

Preferably, the beam portion has a non-uniform cross section, greater at a centre and smaller at the ends.

The orthopaedic pliers are therefore gripped in the manner of medical forceps.

Advantageously, this solution allows the surgeon to grip the device simply and perform stapling rapidly.

According to a further aspect of the invention, at least one centring hole is provided on each lever arm. This hole is provided in order to perform correct centring of the device and the staple to be applied. According to this further aspect of the invention, a first guide wire which pre-bores the seat of the bracket of the orthopaedic staple is inserted inside this centring hole of one of the lever arms so that the other centring hole of the other lever indicates the position where the second hole with the guide wire for the second bracket of the orthopaedic staple will be formed.

According to one aspect of the invention a recess is provided on the beam portion, at each connection portion. The predetermined breakage section is provided inside this recess. According to the present aspect of the invention, also following breakage of the connection portion in order to detach the orthopaedic pliers from the orthopaedic staple, the surface of the beam portion remains uniform in contact with the outer profile.

Advantageously, the present embodiment allows surgeons to lock the orthopaedic pliers in position when it is required to perform insertion so that they may concentrate their attention solely on this delicate operation without having to keep their fingers in a tensioned state.

According to a further preferred aspect of the present invention each lever arm has a lever support element substantially parallel to the beam portion at one end opposite to the ring portion. This element further comprises a bearing portion adapted to make contact with the beam portion of the orthopaedic staple. Owing to the presence of this bearing portion it is possible to obtain a lever effect which favours the equilibrium of the forces acting on each connection portion when the surgeon operates the ring portions, moving the lever arms together.

According to a different aspect of the invention, the insertion brackets are arranged along slightly converging directions, creating an angle of less than 90° with respect to the beam portion. As a result of this position, once the insertion tensioning has been completed, the orthopaedic staple will tend to assume again its original position, compressively pre-loading the two bone stumps.

Nothing prevents to adopt a different form, for example by varying further the angle between the beam portion and the insertion brackets, all of which being included within the scope of protection defined by the accompanying claims.

Furthermore, according to a preferred aspect, the insertion brackets of the orthopaedic staple have a sawtooth profile. This solution allows the insertion brackets to be used as a drilling guide, avoiding the need to use a special drilling guide and therefore an additional element which would make the surgeon's task more time-consuming and more complex.

According to a further aspect of the invention, the stapler is made of a material with a highly elastic property. This elastic property in fact allows recovery of the tension after a stressed state, ensuring a suitable pre-loaded state once the orthopaedic staple and orthopaedic pliers have been removed. In particular, a preferred aspect envisages the use of titanium alloys, the elastic coefficient of which is higher than that for example of stainless steel. Nothing prevents, however, to use different materials, which are included within the scope defined by the accompanying claims.

According to a preferred aspect of the invention the beam portion is arch-shaped so as to recover further elastoplastic deformation during the approach phase of the lever arms of the orthopaedic pliers and consequent straightening of the two insertion brackets.

Further characteristic features and advantages of the orthopaedic stapler according to the present invention will emerge from the description, provided hereinbelow, of a preferred example of embodiment provided by way of a non-limiting example with reference to the accompanying drawings.

BRIEF DESCRIPTION OF THE FIGURES

In the different figures, similar elements will be identified by similar reference numbers.

DETAILED DESCRIPTION

Figure 1:
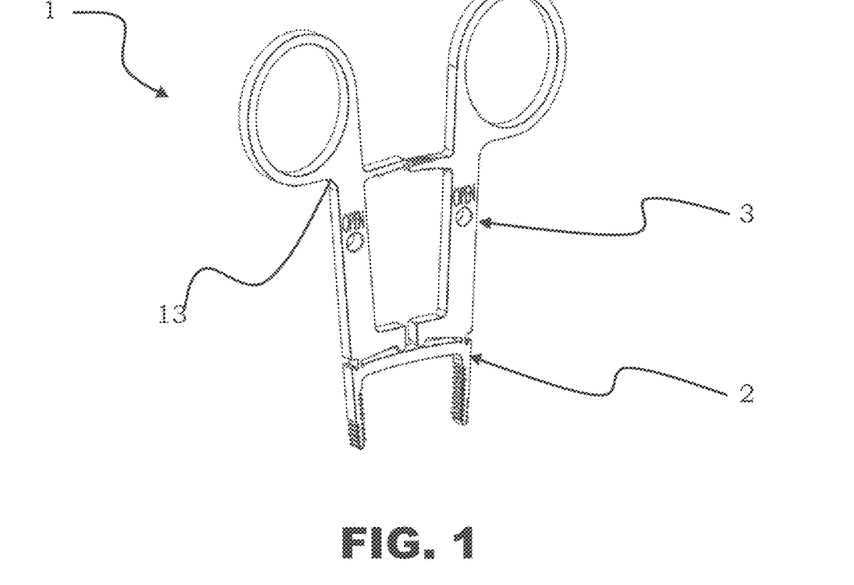
FIG. 1 shows a perspective view of the orthopaedic stapler according to the present invention.
Figure 2:
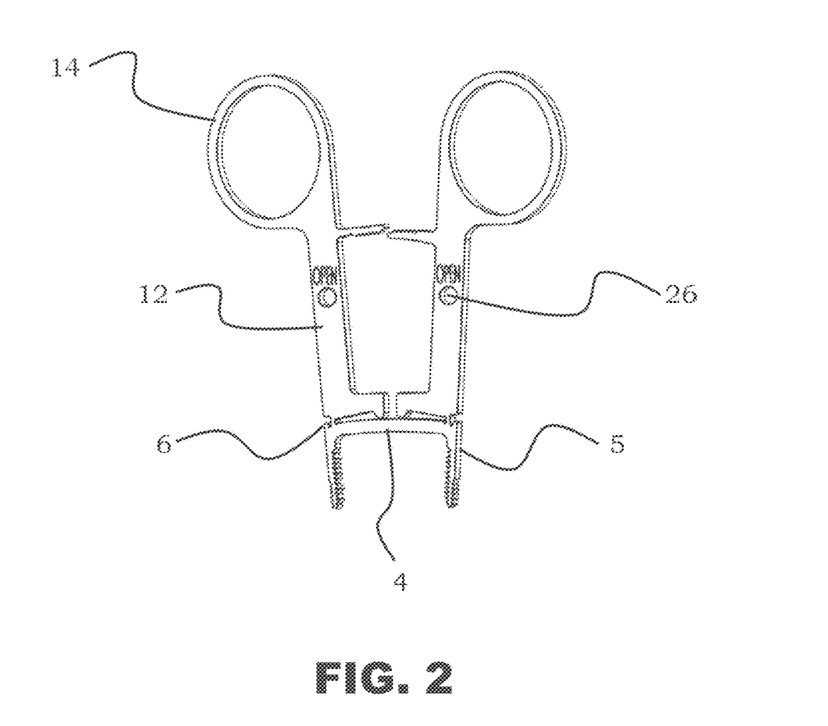
FIG. 2 shows a front view of the orthopaedic stapler according to FIG. 1.

With reference to attached FIGS. 1 and 2, 1 denotes overall and in schematic form an orthopaedic stapler provided in accordance with the present invention.

The orthopaedic stapler 1 comprises an orthopaedic staple 2 and orthopaedic pliers 3.

The orthopaedic staple 2 comprises a beam portion 4 and two insertion brackets 5 each connected integrally to an end 6 of the beam portion 4. Basically the orthopaedic staple 2 is substantially U-shaped. In the present embodiment the beam portion 4 is arch-shaped. Furthermore, in the present embodiment the insertion brackets 5 are directed along two directions slightly converging in a rest condition, creating an angle of less than 90° with respect to the beam portion 4. The orthopaedic pliers 3 comprise two lever arms 12. Each lever arm 12 has at an end 13 opposite to the orthopaedic staple 2 a ring portion 14. The ring portion 14 allows the surgeon to insert his/her fingers to use the orthopaedic stapler 1 in the manner of medical forceps.

In the present embodiment each lever arm 12 is provided with a centring hole 26. This centring hole 26 is a hole passing through the thickness of the orthopaedic stapler 1. The centring holes 26 are designed to receive guide wires used for pre-drilling of the bone, allowing positioning of the holes inside which the insertion brackets 5 will be inserted.

Figure 3:
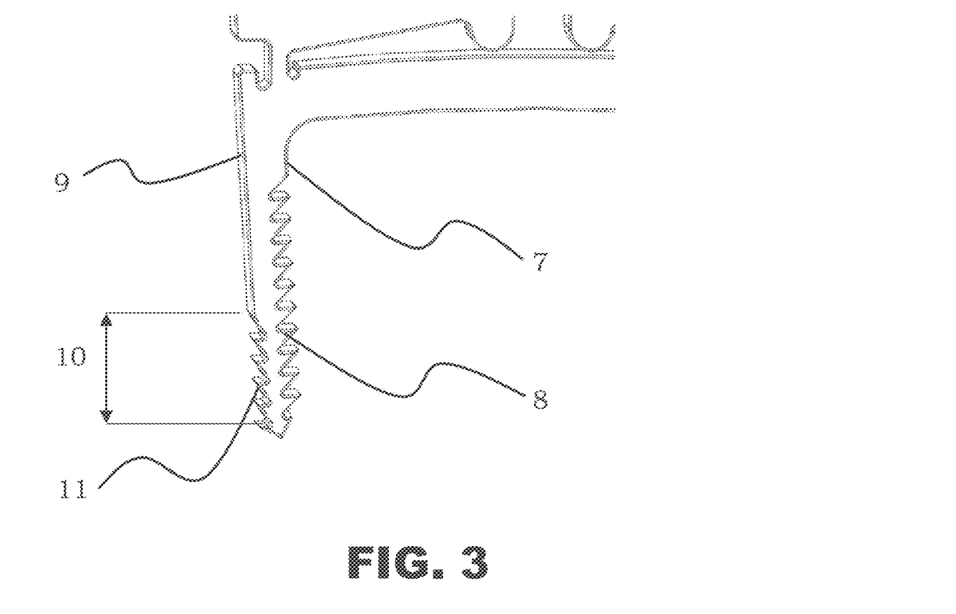
FIG. 3 shows a detail of the insertion bracket of the orthopaedic stapler according to FIG. 1.

As can be seen in FIG. 3, the internal surfaces 7 of the insertion brackets 5 facing each other each have preferably a sawtooth profile 8 for acting as a drilling guide, facilitating insertion but at the same time preventing undesirable removal of the brackets 5 from the respective seats formed in the bone. Furthermore, the external surfaces 9 of the insertion brackets 5, opposite to the internal surfaces 7, preferably have a profile section 10 with a sawtooth profile 11, with an effect similar to that of the sawtooth profiles 8.

Figure 4:
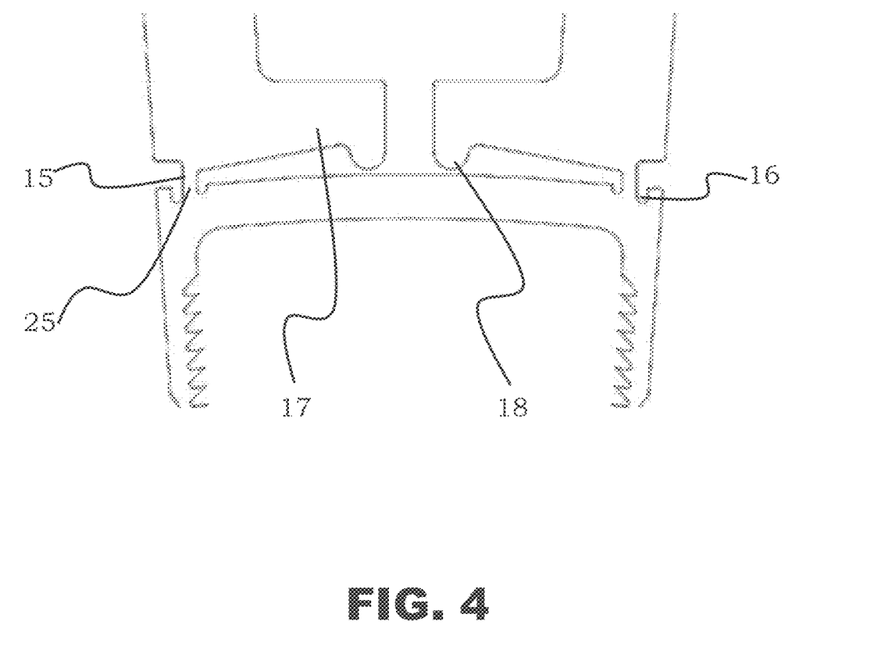
FIG. 4 shows a detail of the connection portions of the orthopaedic stapler according to FIG. 1.

As can be seen more clearly in FIG. 4, the orthopaedic pliers 3 are connected to the orthopaedic staple 2 by means of a connection portion 15 provided on each lever arm 12. The connection portions 15 are substantially bridge-pieces and are preferably positioned close to each end 6 of the beam portion 4, opposite to the insertion bracket 5. Even more preferably the beam portion 4 comprises two recesses 16 in the region of the connection portions 15. In this way a section 25 of the connection portion 15 which remains on each orthopaedic staple 2 once the orthopaedic staple 2 and the orthopaedic pliers 3 have been separated is contained within the recess 16 and the surface of the beam portion 4 in contact with the outer profile is uniform.

Figure 5:
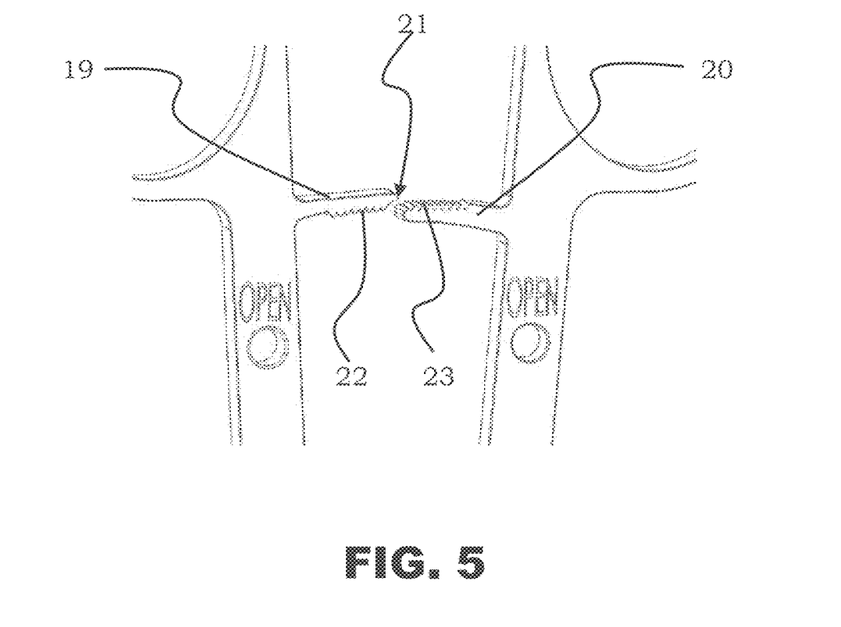
FIG. 5 shows a detail of the engaging mechanism of the orthopaedic stapler according to FIG. 1.

Furthermore, the lever arms 12 have two lever support elements 17 at the end opposite to the ring portion 14 and substantially parallel to the beam portion 4. Each lever support element 17 is directed towards the other lever arm 12. In other words, the lever arms 12 assume the form of two L-shaped profiles facing each other. The lever support elements 17 comprise two bearing portions 18 in contact with the beam portion 4 in the vicinity of the middle section of the beam portion 4. The bearing portions 18 in the present embodiment act to ensure the equilibrium of the force applied by the surgeon on the ring portions 14 during the movement of the lever arms 12 towards each other. In the present embodiment, as can be clearly seen in FIG. 5, the lever arms 12 of the orthopaedic pliers 3 comprise a first projecting element 19 and a second projecting element 20, the first projecting element 19 on one lever arm 12 being directed towards the second projecting element 20 of the other lever arm 12. The first projecting element 19 and the second projecting element 20 have a reciprocal engaging mechanism 21. In the present embodiment provided by way of a non-limiting example, the engaging mechanism 21 consists of two complementary sawtooth profiles 22 and 23, respectively provided on the profiles of the first projecting element 19 and the second projecting element 20 and directed towards each other. Nothing prevents to adopt different forms of the teeth or a different engaging mechanism 21.

Figure 6:
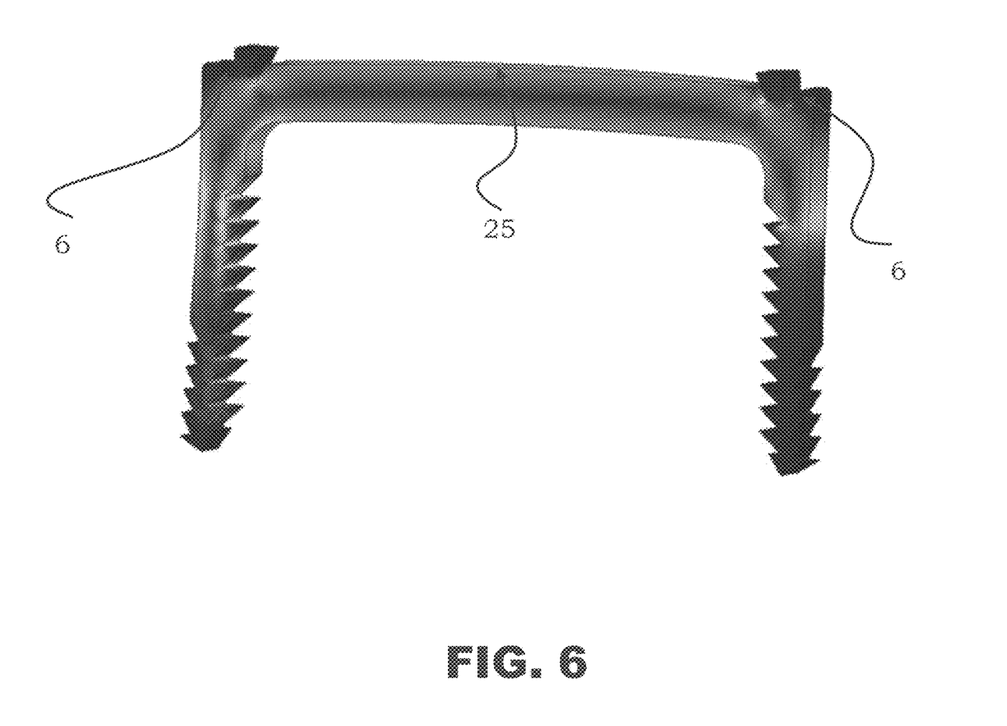
FIG. 6 shows a perspective view of the orthopaedic staple od FIG. 1.
Figure 7:
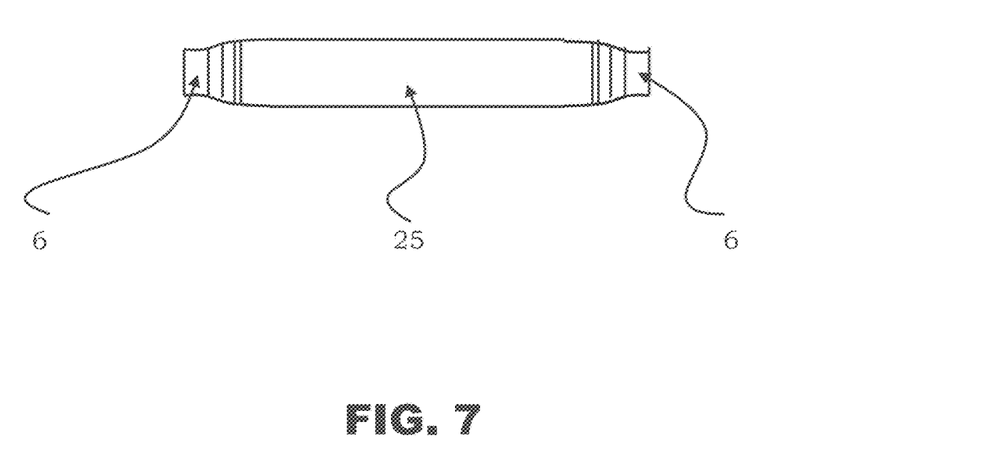
FIG. 7 shows a top view of the orthopaedic staple of FIG. 8.

As can be seen in FIGS. 6 and 7 the beam portion 4 has preferably a non-uniform cross section, greater at a centre 25 and smaller at the ends 6. Using a non-uniform cross section of the beam portion 4, greater at the centre and smaller at the ends, it is possible to obtain a uniform stress through the beam portion 4 when the bearing portions 18 acts on the beam portion 4.

The functioning of the orthopaedic stapler according to the present invention will be described below considering, for illustrative purposes, the embodiment described above and as clearly shown in FIG. 8.

Figure 8:
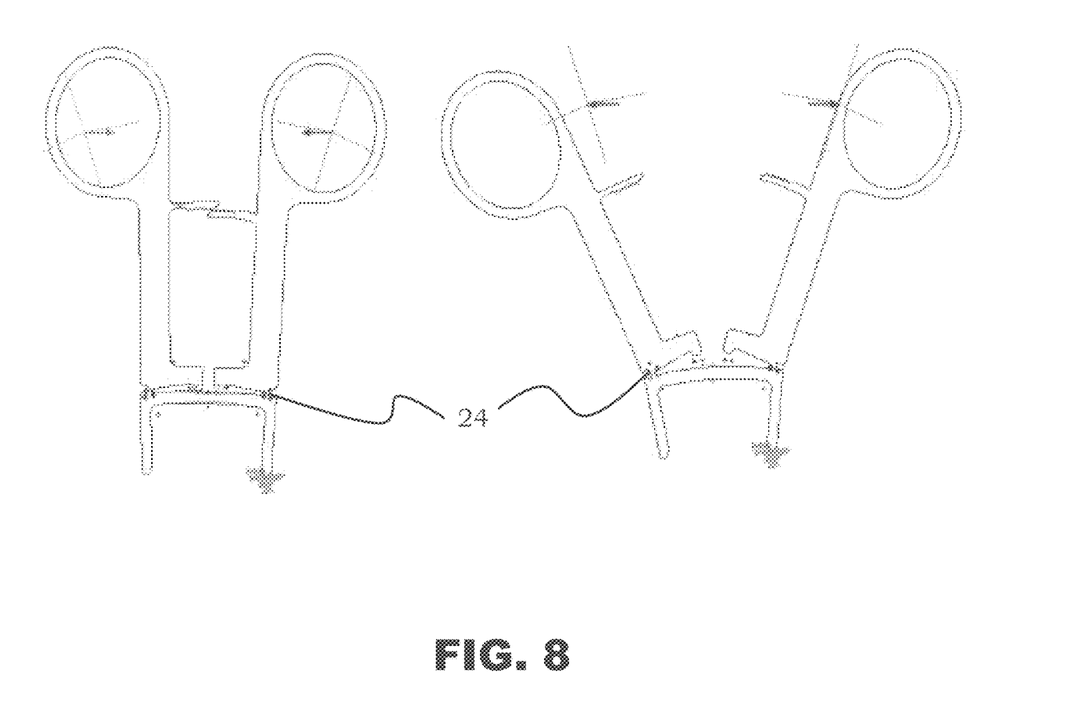
FIG. 8 shows an example of operation of the orthopaedic stapler according to the present invention.

Following osteotomy and positioning of the bone stumps and the bone fragments in the correct position, the surgical procedure involves inserting a first guide wire (not shown) which pre-bores the seat for an insertion bracket 5 of the orthopaedic staple 2. This guide wire is then inserted inside a centring hole 26 of one of the lever arms 12.

In this way the other centring hole 26 of the other lever arm 12 indicates the position where a second hole will be formed using a second guide wire (not shown), this second hole being designed to seat the second bracket 5 of the orthopaedic staple 2. Once both the initial holes have been formed, the first guide wire and the second guide wire are extracted.

The surgeon applies pressure on the two ring elements 14 moving the two lever arms 12 towards each other and at the same time straightening the insertion brackets 5 which move along two parallel directions. During this step the closing force applied by the surgeon on the ring portions 14, considering the distance from the connection portion 15, is equally balanced as a result of the torque generated by the pulling force on the connection portion 15 and the compression applied by the bearing portions 18. In other words, the bending load applied by surgeon's fingers on the ring portions 14 is transmitted as a pair of forces between the connection portions 15 and the bearing portions 18, reducing the stress at the connection portions 15 to a purely tensile load. Furthermore, in the present embodiment, during this step the engaging mechanism 21 is operated. The teeth of the complementary sawtooth profiles 22 and 23 are then coupled together in a positive engagement. In this way the position defined by the surgeon may be maintained without having to keep a constant pressure on the ring portions 14 using the fingers. The surgeon may therefore concentrate on correctly introducing the orthopaedic staple 2 inside the bone stumps in the region of the fracture. It should be noted that the sawtooth profiles 22 and 23 must be formed taking into account the difference in behaviour and the elastic deformation enduring by the orthopaedic staple 2 carried by the two bearing sections 18 during application of the elastic load.

Once the insertion step has been completed the surgeon disengages by means of a light pressure in the opposite direction the teeth of the sawtooth profiles 22 and 23 of the engaging mechanism 21. In the case of a different form of the teeth or a different engaging mechanism a different operation may be clearly performed. If a pressure is continued to be exerted on the two lever arms 12 so as to move them away from each other the stress acting on the connection portions 15 is completely of a flexural nature and is now greater than the breaking strength of the material of the connection portion 15. Consequently separation occurs along a predetermined breakage section 24 between the orthopaedic staple 2 and the orthopaedic pliers 3. In the present embodiment each section 25 of the connection portions 15 remains inside the recess 16 formed in the beam portion 4, ensuring that a uniform surface is maintained.

The orthopaedic staple therefore remains inside the bone, tending to return, in the case of the embodiment shown, into the rest configuration, namely the configuration where the insertion brackets 5 are slightly converging. This condition therefore gives rise a state where a compressive load acts on the bone stumps.

The present invention solves the technical problem and achieves numerous advantages, the main one of which is certainly that of being able to insert the insertion brackets 5 of the staple 2 in a simple manner and at the same time release them in the desired position with an intuitive movement and without any handling difficulty.

Advantageously the entire operation may be performed by the surgeon using only one hand and without there being any imprecision during application.

A further advantage consists in the fact that the form of the staple is such that a compressive load acting on the fracture between the stumps and bone fragments is generated by the surgeon when operating the orthopaedic stapler 1.

For this reason advantageously materials with a high elasticity are used, so as to allow complete elastic recovery of the tension following the stressing state.

Another advantage is that the insertion brackets 5 have a profile such that they may be used as drilling guides, without having to use a specially designed instrument. Everything needed to perform application of the orthopaedic staple 2, apart from the guide wires, is included in the orthopaedic stapler 1, making it easier to use and reducing its cost.

A further advantage consists in the fact the entire orthopaedic stapler 1 is made from a single metal sheet by means of cutting. This cutting operation may be performed using various techniques, for example laser cutting, water-jet cutting or cutting by means of an electrochemical process, or the like. The possibility of obtaining the entire device by means of a single cutting operation reduces the complications during production as well as the production time and costs. The stapler according to the invention may, however, be made by means of moulding using a synthesis material.

Finally, an advantage of the orthopaedic stapler according to the invention is the possibility that it may be designed with dimensions depending on the specific requirements without affecting operation thereof.

The person skilled in the art will clearly understand that the system according to the present invention may be subject to modifications and variants, all of which fall within the scope of the invention defined by the accompanying claims.

The invention claimed is:

1. Orthopaedic stapler comprising:
    orthopaedic pliers and an orthopaedic staple integrally formed at the distal ends of the pliers,
        said orthopaedic staple comprising:
            a beam portion;
            two insertion brackets at two opposite ends of said beam portion and transverse with respect to said beam portion, said beam portion having a non-uniform cross section between the two insertion brackets, greater at a centre and smaller at the two opposite ends;
        said orthopaedic pliers comprising two lever arms integrally connected to said orthopaedic staple by means of connection portions at the two opposite ends of the beam portion;
        said connection portions being breakable along predetermined breakage sections;
    wherein at least one lever arm comprises a ring portion at one end and said lever arms comprise at least one first projecting element, at least one second projecting element, said first projecting element on one lever arm being directed towards said second projecting element on the other lever arm, said first projecting element and said second projecting element being provided with a reciprocal engaging mechanism;
    wherein each of said lever arms comprises at least one centring hole for inserting a pre-drilling guide wire;
    wherein said beam portion comprises two recesses at said connection portions, and wherein said predetermined breakage sections are internal to said recesses of said beam portion; and
    wherein each of said lever arms has a lever support element parallel to said beam portion at one end opposite to said ring portion, said lever support element further comprising a bearing portion adapted to make contact with said beam portion of said orthopaedic staple.

2. Orthopaedic stapler according to claim 1, wherein said reciprocal engaging mechanism comprises a sawtooth profile along said first projecting element and a corresponding sawtooth profile along said second projecting element.

3. Orthopaedic stapler according to claim 1, wherein said beam portion is arch-shaped.

4. Orthopaedic stapler according to claim 1, wherein said insertion brackets are arranged along slightly converging directions, creating an angle of less than 90° with respect to said beam portion.

5. Orthopaedic stapler according to claim 1, wherein said insertion brackets have a sawtooth profile acting as a drilling guide.

6. Orthopaedic stapler according to claim 1, wherein said orthopaedic stapler is made of a material adapted to recover a tension after a stressed state.

7. The orthopaedic stapler of claim 1, wherein said reciprocal engaging mechanism comprises a sawtooth profile along said first projecting element and a corresponding sawtooth profile along said second projecting element.

8. The orthopaedic stapler of claim 1, wherein said orthopaedic stapler is made of a material adapted to recover a tension after a stressed state.

9. Orthopaedic stapler comprising:
    an orthopaedic pliers;
    an orthopaedic staple integrally formed at the distal ends of the pliers;

said orthopaedic staple comprising:
  a beam portion;
  two insertion brackets extended transversally at two opposite ends of the beam portion, said beam portion having a non-uniform cross section between the two insertion brackets, greater at a centre and smaller at the two opposite ends;
said orthopaedic pliers further comprising two lever arms each integrally connected to a corresponding end of said beam portion by means of a breakable connection portion;
a ring portion located at one end of at least one of said lever arms;
a first projecting element formed on one of said lever arms;
a second projecting element formed on the other of said lever arms;
said first projecting element being extended towards said second projecting element; both projecting elements being provided with a reciprocal engaging mechanism; and
wherein each of said lever arms comprises at least one centring hole for inserting a pre-drilling guide wire.

10. The orthopaedic stapler of claim 9, wherein said beam portion comprises two opposite recesses forming breakable connection portions, and wherein each breakable connection portion include a breakage section located internally to the recess of the beam portion.

11. The orthopaedic stapler of claim 9, wherein each of said lever arms has a lever support element parallel to said beam portion at one end opposite to said ring portion, said lever support element further comprising a bearing portion adapted to make contact with said beam portion of said orthopaedic staple.

12. The orthopaedic stapler of claim 9, wherein said beam portion is arch-shaped.

13. The orthopaedic stapler of claim 9, wherein said insertion brackets are arranged along slightly converging directions, creating an angle of less than 90° with respect to said beam portion.

14. The orthopaedic stapler of claim 9, wherein said insertion brackets have a sawtooth profile acting as a drilling guide.

* * * * *